United States Patent [19]

Beitzel

[11] 4,189,363
[45] Feb. 19, 1980

[54] PROCESS OF PRODUCING OZONE IN WATER

[75] Inventor: Stuart S. Beitzel, Santa Ana, Calif.

[73] Assignee: Stuart Enterprises, Santa Ana, Calif.

[21] Appl. No.: 13,145

[22] Filed: Feb. 21, 1979

[51] Int. Cl.² ............................ A61L 1/00; B01J 1/10; C01K 1/00
[52] U.S. Cl. .............................. 204/157.1 R; 250/527; 422/23; 422/24; 422/186
[58] Field of Search ................. 204/157.1 R; 250/527; 422/23, 24, 186

[56] References Cited

U.S. PATENT DOCUMENTS

| | | | |
|---|---|---|---|
| 3,576,733 | 4/1971 | Beitzel | 204/320 |
| 3,775,314 | 11/1973 | Beitzel et al. | 210/63 |
| 4,045,316 | 8/1977 | Legan | 204/157.1 R |

Primary Examiner—Howard S. Williams
Attorney, Agent, or Firm—Edward D. O'Brian

[57] ABSTRACT

Water may be purified through the utilization of ultraviolet light and ozone so as to obtain some residual ozone in the water treated by passing a mixture of water and air or air and ozone through a nozzle which concurrently compresses the mixture and breaks up any gas bubbles within the mixture into what may be loosely referred to as a radiation housing or chamber. The housing is a hollow, cylindrical chamber located around an elongated tubular lamp for producing actinic light such as ultraviolet light. The mixture is introduced into this chamber in a substantially tangential manner so as to swirl around the interior chamber in passing from the inlet of the chamber where the nozzle is located to the outlet of the chamber at the other end of the chamber.

12 Claims, 2 Drawing Figures

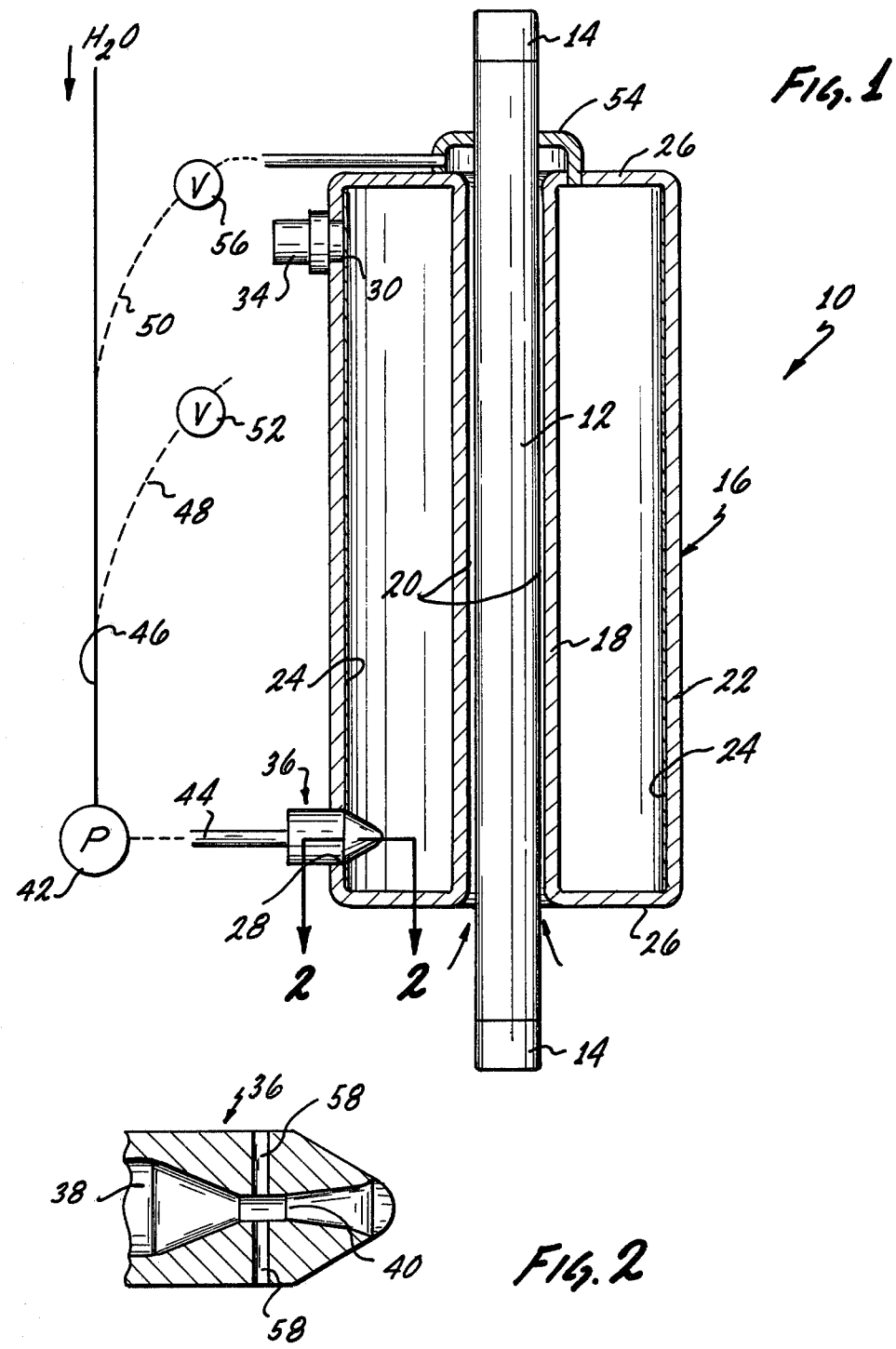

PROCESS OF PRODUCING OZONE IN WATER

BACKGROUND OF THE INVENTION

The invention set forth in this specification is specifically directed to the purification of water by the use of ozone and ultraviolet light. It is, however, considered that the broader or generic aspects of the invention are applicable in connection with the treatment of different liquid-gas mixtures in the presence of actinic light.

In the past a number of different devices or apparatuses have been developed and used for the purpose of exposing various different liquids and gas-liquid mixtures to actinic light such as ultraviolet light. Such devices have been utilized to a limited extent in the treatment of water. On occasion such devices have been utilized in promoting various different chemical reactions the nature of which have, of course, been dependent upon the reactant or reactants exposed to actinic or similar radiation.

It is considered that such prior devices and methods have not been widely utilized in treating water so as to render such water potable to any significant extent because of several factors, all of which may be loosely grouped together under the heading "efficiency".

This term "efficiency" is utilized herein in a broad, generic sense so as to include interrelated factors such as the economics of purifying water so that it is potable but in addition is employed so as to include the effectiveness of such treatment so that the water treated will remain substantially "pure" in the sense that it is free from bacterial and viral contamination during reasonable storage. It is believed that methods and apparatuses as have previously been known for use in treating water with actinic radiation such as ultraviolet light have in general not been sufficiently effective or efficient for their intended purpose so as to be acceptable from a commercial standpoint for use in comparatively small units or installations away from domestic and similar water supplies.

SUMMARY OF THE INVENTION

A broad objective of the present invention is to provide both a new and improved method and a new and improved apparatus for the treatment of liquid-gas mixtures in the presence of actinic light. More specifically the invention is intended to provide a new and improved method and apparatus for treating water through the use of ozone produced as a result of the action of actinic light so as to render such water potable by killing bacteria and viruses present within such water. A further objective of the invention is to provide a method and apparatus as described which can be utilized to provide a degree of residual ozone in the water treated so that such water is capable of being stored for a reasonable period prior to its use and will remain substantially "pure" in the sense that it is free from bacterial and viral contamination during such storage. The precise duration of such period will, of course, be dependent upon many factors.

A further objective of the present invention is to provide an apparatus as herein described which may be utilized to practice the process herein indicated, which is of a sufficiently small physical dimension so as to be capable of being utilized in drinking fountains, in recreational vehicles or similar vehicles, on board comparatively small boats and ships, or in other installations. A further broad objective of the invention is to provide a method and apparatus which are relatively "efficient" in the broad or generic sense in which the term "efficiency" was used in the preceding discussion.

Those objectives of the present invention related to an apparatus are achieved by providing an apparatus having a centrally located, elongated tubular lamp for producing actinic radiation and a generally cylindrical housing located concentrically around the lamp, the housing including a centrally located tube capable of transmitting radiation into the interior of the housing located around and immediately adjacent to the lamp, the housing also including an inlet leading into one end of the housing and an outlet leading from the other end of the housing in which the improvement comprises: nozzle means located generally within the inlet for concurrently compressing a gas-liquid mixture conveyed to the nozzle means and the inlet and for breaking up air bubbles within the mixture so that they are smaller than about 0.5 mm. in diameter, the nozzle means being located so that the gas-liquid mixture emitted from it swirls in a spiral manner around the interior of the housing as it passes from the inlet to the outlet of the housing.

Those objectives of the present invention related to the process of the invention are achieved by providing a process for exposing a gas-liquid mixture to actinic light in which the improvement comprises: compressing a gas-liquid mixture while concurrently breaking up any gas bubbles within the mixture under such conditions that the mixture at the time it is compressed and at the time the bubbles are broken up are subject to turbulence and a shearing type action so as to produce a gas-liquid mixture in which the broken up gas bubbles are less than about 0.5 mm. in diameter and swirling the so produced gas-liquid mixture in a spiral manner around a source of actinic radiation under such conditions that there is turbulence within the mixture.

BRIEF DESCRIPTION OF THE DRAWING

Because of the nature of this invention it is considered that it is best more fully described with reference to the accompanying drawing in which:

FIG. 1 indicates a presently preferred apparatus for practicing the invention, a part of this apparatus being shown diagrammatically and another part of this apparatus being shown in cross-section;

FIG. 2 is a partial cross-sectional view taken at line 2—2 of FIG. 1.

The invention set forth in this specification involves the concepts or principles verbally expressed in the appended claims which are considered to form a part of this specification. From a consideration of these claims those familiar with the field of the invention will realize that these concepts or principles can be utilized in different manners in connection with somewhat differently constructed and somewhat differently appearing apparatuses.

DETAILED DESCRIPTION

In the drawing there is shown an apparatus 10 for use in the purification of water through the use of ozone but which also may be employed for other purposes. This apparatus 10 includes a centrally located, elongated, tubular, cylindrical lamp 12 of a type commonly employed for producing ultraviolet radiation or other similar radiation. For convenience the usual terminals which are normally attached to the ends 14 of the lamp 12 for the purpose of supplying current and for the purpose of supporting it are not illustrated since these are of a conventional character.

This lamp 12 is used with a generally cylindrical housing 16 constructed so as to include a centrally located cylindrical tube 18 capable of transmitting the radiation emitted during the operation of the lamp 12. This tube 18 is located concentrically around the lamp 12 intermediate the ends 14. It is preferably spaced a short distance from the exterior of the lamp 12 as shown in order to provide a cylindrical gap or air space 20 between the lamp 12 and the tube 18. Such a gap 20 is commonly utilized in prior apparatus closely related to the apparatus 10 as a barrier to prevent thermal shock as the result of differences in the temperatures of the lamp 12 and of the tube 18. With the apparatus 10 this gap 20 is preferably utilized for a secondary purpose as hereinafter explained.

The housing 16 also includes an outer cylindrical wall 22 located concentrically around the tube 18 so as to be spaced from the tube 18. Preferably a lining 24 of a material capable of reflecting the radiation from the lamp 12 is located completely around the interior of this wall 22. The lining 24 may be conveniently made of material such as polished stainless steel or the like. Although the precise spacing of the wall 22 from the tube 18 is not critical the wall 22 should be sufficiently close to the tube 18 so as to tend to promote a flow pattern within the housing 16 as hereinafter described. This housing 16 also includes ends 26 extending between the tube 18 and the wall 22.

An inlet opening 28 is located in the wall 22 immediately adjacent to one of the ends 26 and an outlet opening 30 is located within the wall 22 immediately adjacent to the other of the ends 26. An appropriate conventional piping type fitting 34 is located in the outlet opening 30 for the purpose of conveying liquid from within the interior of the housing 16. A specialized nozzle 36 is located within the inlet opening 28 for the purpose of conveying a gas-liquid mixture—normally a water-air or a water, air and ozone mixture—into the interior of the nozzle 36.

This nozzle 36 is constructed so as to include an elongated passage 38 which is preferably shaped in the well known manner of a venturi tube so as to have an internal constriction or throat 40. The nozzle 36 is mounted in the inlet opening 28 as illustrated so that this passage 38 extends substantially tangentially to the axis (not shown) of the lamp 12 and the housing 16 and so that it extends substantially parallel to the adjacent end 26 or upwardly from the end 26 at a slight angle to the end 26 a short distance from this end 26.

Technically the passage 38 is located tangentially to a radius which is of such a length as to be smaller than a radius extending from the axis (not shown) of the lamp 12 to the wall 22 and which is greater than the radius extending from this same axis to the exterior of the tube 18 within the housing 16. This is so that during the use of the apparatus 10 as a mixture as noted herein is forced under pressure into the housing 16 this mixture will be set in motion so as to swirl around the tube 18 within the housing 16 in what may be referred to as a spiral manner as it passes from the inlet opening 20 to the outlet opening 30.

In the apparatus 10 a gas-liquid mixture as indicated in the preceding is normally supplied by a conventional pump 42 through a line 44 to the nozzle 36. This pump 42 is normally connected so as to draw liquid such as water through another line 46 which may be connected to either or both of two different side lines or laterals 48 and 50 in such a manner that during the normal operation of the pump 42 this pump 42 will draw a gas into the water flowing through the line 46 through either or both of the laterals 48 and 50. The concept of a gas being drawn into a line conveying a fluid as fluid is moved through the line is so well known that it is not considered that there is any necessity to discuss the manner of operation involved here in connection with the use of the laterals 48 and 50.

When the lateral 48 is open to the ambient air adjacent to the apparatus 10 such air can be drawn into the system described. A common conventional valve 52 is preferably used with this lateral 48 so that it can be closed off. The lateral 50 is connected to what may be referred to as a hood or shroud 54 located against an end 26 of the housing 16 and against the lamp 12. Another valve 56 is located in the lateral 50 so that this lateral 50 may be also closed off. When the valve 56 is open and when the valve 52 is closed the operation of the pump 42 will cause air to be drawn into the line 46 as indicated in the preceding from the gap 20 between the tube 18 and the lamp 12.

As the lamp 12 is operated and as air is moved in this manner ultraviolet light from the lamp 12 will tend to kill bacteria and viruses in a conventional manner. Concurrently this light will cause the oxygen in such air to react with itself in a well known manner so as to form ozone in an amount which will be dependent upon a number of variables, the dimensions of the gap 20, the speed with which it is moved through the gap 20, the temperature conditions prevailing within this gap 20 and the like. A small amount of a catalyst for the production of ozone (not shown) insufficient to significantly affect ultraviolet light transmission may even be present in this gap 20. Although such air movement unquestionably will result in some cooling of the lamp 12 such cooling is not considered to be significant enough to normally affect the performance of the lamp 12.

The apparatus 10 may be operated so that either an ozone-air mixture created within the gap 20 or ambient air may be drawn into the line 46 as the pump 42 is operated. It is, of course, possible by opening both of the valves 52 and 56 so as to draw both ambient air and an ozone-air mixture as indicated into the line 46. The gas drawn into the line 46 will, of course, be mixed to a degree with the liquid—normally water—present within the line 46. Further mixing will, of course, occur as the result of the operation of the pump 42.

In general the degree of such mixing of a type beneficial to the invention will be enhanced if this pump 42 is of a type capable of exercising a significant shearing type action such as, for example, a rotary vane type pump. Further mixing will, of course, occur as the mixture moves through the line 44 toward and into the nozzle 36. Such mixing will be promoted by the normal turbulence present. As there is such mixing some of the oxygen or ozone will, of course, tend to be taken up within the liquid present. This action is of a type corresponding to what is commonly referred to as aeration in connection with exposing water to ambient air.

The actions indicated in the preceding discussion continue as a mixture as described in the preceding reaches the nozzle 36. Within this nozzle 36 the mixture will be constricted as it passes to the constriction or throat 40 and then the pressure on the mixture will be relieved to a degree depending upon the outlet pressure maintained at the outlet opening 30. This nozzle 36 serves several important functions. Because of the action of the throat 40 and the manner of flow within this throat 40 it is considered that the nozzle 36 tends to further break up so as to reduce in size any gas bubbles present in the mixture. Concurrently as the mixture moves through the throat 40 such bubbles are compressed as they are formed from larger bubbles. It is considered that such formation of comparatively small bubbles is promoted by what may be referred to as a shearing action occurring as the mixture moves through the constriction or throat 40.

As a result of the operation of the nozzle 36 as indicated in the preceding the mixture emitted into the housing 16 from the nozzle 36 in many respects can be compared with carbonated water such as is utilized in many soft drinks. Extremely small bubbles or pockets of gas will be present in the stream emitted from the nozzle 36. This mixture may be loosely referred to as pin-point type bubbles. The precise dimensions of these bubbles cannot be readily determined. They should be as small as reasonably possible to obtain. On the basis of visual comparison it is considered that they are significantly smaller than 0.05 mm. in diameter. As far as the invention is concerned the smaller the size of these bubbles the better in providing as great a surface area as possible between any gas present and liquid since various reactions produced between ozone present in these bubbles or produced within these bubbles takes place substantially at the surfaces of these bubbles.

It has been discovered that the breaking up of gas bubbles so as to obtain an extremely fine dispersion can be accentuated or improved by locating within the nozzle 36 at least one and preferably a plurality of auxiliary passages 58 which extend from the interior of the housing 16 through the nozzle 36 so as to intersect the constriction 40 at about the region of maximum reduction in cross-sectional dimension within the passage 38. These auxiliary passages 58 preferably extend radially in the nozzle 36 and are preferably located so as to intersect the constriction 40 equidistant from one another. During the operation of the apparatus 10 as described a liquid-gas mixture from within the housing 16 will be drawn through these auxiliary passages 58 into the throat 50 as a result of the velocity of flow through the passage 38. The flow through the auxiliary passages 58 will mix with the flow through the constriction 40 so as to obtain an intimate mixture.

As a result of the tangential orientation of the nozzle 36 within the housing 16 flow will be as described within the housing 16 in a substantially swirling manner around the lamp 12 toward the outlet opening 30 during the operation of the apparatus 10 as described. However, when as preferred the auxiliary passages 58 are used the flow will not be of a "pure" swirling-type flow. Significant turbulence will be present within the housing 16, particularly adjacent to the nozzle 36 where there is a feedback through the auxiliary passages 58. Such turbulence is considered to be of importance in facilitating contact between virtually all of the liquid present with gas bubbles or pockets at the surfaces of such bubbles or pockets.

This is, of course, related to what may be regarded as the entire "action" achieved within the housing 16 as the apparatus 10 is operated. As a liquid-gas mixture moves in the manner described from the inlet opening 28 to the outlet opening 30 this mixture will be exposed to radiation from the lamp 12. Such radiation as completely passes through the interior of the housing 16 will be reflected by the lining 24 back through the mixture within the housing 16. As the radiation is used in this manner it will, of course, cause reactions which are dependent upon the materials present.

When the apparatus 10 is used in the intended, preferred manner these materials will be water and air or an air-ozone mixture. As such as water-gaseous mixture passes through the housing 16 ultraviolet radiation from the lamp 12 will, of course, cause the formation of ozone from the oxygen present. As a result of the turbulence such ozone will be available at the surfaces or interfaces of the gas bubbles and the liquid present so as to react with organic matter such as bacteria or viruses present within the water. Because of the turbulent, swirling movement present the liquid exposed to the gaseous-ozone will in effect be constantly changed. As a result of this a good, effective mixing action will be achieved which will promote the ozone produced oxidizing organic matter and/or to attack bacteria and viruses. Further, the ozone available for this purpose will continuously be produced in the water-gas mixture during substantially the entire time that this mixture is within the housing 16.

It is considered significant that the ozone produced in the manner described tends to be "fixed" in the water in the sense that such ozone does not decompose in the water as rapidly as ozone normally deteriorates to normal oxygen. Obviously the duration of the time when ozone can be detected in water processed using the apparatus 10 will be dependent upon many factors. It is considered that the temperature at which such water is stored is quite important in this regard and that the higher the temperature the more rapidly evidence of ozone being present within it disappears. Of course, water processed using the apparatus 10 will not contain residual ozone in those cases where the water is so highly contaminated with organic matter that complete oxidation of such organic matter will not take place within the housing 16.

It is considered that the use of two inlets—the laterals 48 and 50—for introducing either ambient air or an air-ozone mixture in the water being treated is significant in several regards. This provides for a variation in the operation of the apparatus 10 which may be desirable for certain types of water supplies. Obviously either or both of the laterals 48 or 50 can be employed with the invention.

The use of the lateral 50 to convey an ozone-air mixture is considered to be quite preferable in the case in which a water supply is quite contaminated with organic material since some ozone "enters the system" prior to a water-gas mixture entering the housing 16. This provides an opportunity for oxidation to take place outside of the housing 16 so that the oxidation within this housing 16 essentially finishes the oxidation taking place prior to the mixture being forced into the housing 16. This utilization of an ozone-air mixture is also considered significant since in prior related apparatuses some ozone has been produced in the area surrounding an ultraviolet tube tending to isolate the tube from a treatment vessel or housing and since in such prior apparatuses such limited amounts of ozone have not been utilized. With the present invention such amounts of ozone can be utilized by recirculating as described.

At times the reasonably long, yet inherently somewhat short period that evidence of ozone will remain in water processed as indicated in the preceding after the storage of such water will be inadequate for some purposes. In these cases it is possible to place in solution in the water being treated in accordance with this invention a comparatively small quantity of cyanuric acid or an equivalent compound which is substantially incapable of being oxidized by ozone under normal conditions and which will tend to form a complex with ozone which will exhibit the properties of ozone for a prolonged period. The shearing action achieved under pressure conditions by the nozzle 36 is considered to aid in the formation of such a complex and, indeed, is considered to tend to stabilize ozone passing into or through the nozzle 36 even in the absence of such a complexing agent. It is considered that in most applications where the invention is intended to be used such as in drinking fountains and the like that the use of such a complexing agent is not reasonably necessary.

It is not to be assumed from this specification that the treatment indicated herein is the only or all the treatment which may be needed in making a particular water or water mixture potable. On many occasions water treated as herein described is best filtered and frequently should be passed through an absorbing bed such as an activated charcoal bed prior to being utilized. Frequently it may be necessary to otherwise purify such water as, for example, by known reverse osmosis techniques. In order to avoid possible damage to a reverse osmosis membrane because of the presence of residual ozone preferably water treated using reverse osmosis should be so treated prior to being processed in the apparatus 10.

The relative amounts of air or of an air-ozone mixture which should be utilized in connection with any specific amount of water may, of course, be varied depending upon specific conditions present. At present it is considered that from about 1 to about 2 parts by weight of either or both of such gas mixtures should normally be utilized per 100 parts by weight of water in utilizing an apparatus such as the appartus 10. One factor which is important in determining the amount of a gas mixture used in connection with any specific amount of water will be the amount of organic material capable of being oxidized present. Another factor will, of course, be the dwell time of a liquid-gas mixture within the housing 16. If this dwell time is so short that a residual of ozone is not present within the treated liquid-gas mixture such a mixture may, of course, be recycled through the housing 16. This is not normally considered to be necessary because the nozzle 36 described mixes in such a manner as to cause turbulence so as to cause an effect corresponding to a degree to recycling treated fluid through the housing 16.

I claim:

1. An apparatus having a centrally located, elongated, tubular lamp for producing actinic radiation and a generally cylindrical housing located concentrically around said lamp, said housing including a centrally located tube capable of transmitting radiation into the interior of said housing located around and immediately adjacent to said lamp, said housing also including an inlet leading into one end of said housing and an outlet leading from the other end of said housing in which the improvement comprises:

nozzle means located generally within said inlet for concurrently compressing a gas-liquid mixture conveyed to said nozzle means and said inlet and for breaking up gas bubbles within said mixture so that they are smaller than about 0.5 mm. in diameter, said nozzle means being located so that the gas-liquid mixture being emitted from it swirls in a spiral manner around the interior of said housing as it passes from said inlet to said outlet of said housing.

2. An apparatus as claimed in claim 1 wherein:
   said nozzle means includes an elongated passage having a constriction intermediate its ends and includes at least one auxiliary passage leading from the exterior of said nozzle means within said housing so as to intersect said constriction within said passage.

3. An apparatus as claimed in claim 2 wherein:
   there are a plurality of said auxiliary passages located so as to intersect said constriction equidistant from one another around the exterior of said constriction.

4. An apparatus as claimed in claim 1 wherein:
   said nozzle means includes an internal passage having the shape of a venturi tube, said tube including a throat of lesser dimension than the remainder of said passage, and including at least one auxiliary passage leading from the interior of said housing to said throat.

5. An apparatus as claimed in claim 4 including:
   a plurality of said auxiliary passages, said auxiliary passages intersecting said throat completely around said throat.

6. An apparatus as claimed in claims 1, 2 or 4 including:
   pump means for providing a gas-liquid mixture to said inlet.

7. An apparatus as claimed in claims 1, 2 or 4 wherein:
   said tube is spaced from the exterior of said lamp, and including
   pump means for providing a liquid-gas mixture to said inlet,
   means for conveying an ozone-gas mixture from within the space the exterior of said lamp and said tube to said pump means,
   means for conveying a liquid to said pump means.

8. An apparatus as claimed in claim 7 further including:
   means for conveying ambient air to said pump means.

9. A process for exposing a gas-liquid mixture to actinic light by passing said mixture adjacent to an elongated source of actinic light in which the improvement comprises:
   compressing said gas-liquid mixture while concurrently breaking up any gas bubbles within said mixture under such conditions that the mixture at the time it is compressed and at the time the bubbles are broken up are subject to turbulence and a shearing type action so as to produce a gas-liquid mixture in which the broken up gas bubbles are less than about 0.5 mm. in diameter, and
   swirling the so produced gas-liquid mixture in a spiral manner around a source of actinic light in such a manner that the mixture as it is swirling travels along the length of said source of light and under such conditions that there is turbulence within said mixture.

10. A process as claimed in claim 9 wherein:
    said gas-liquid mixture is compressed and gas bubbles within said mixture are broken up by passing said mixture under pressure through a passage in a nozzle having a constriction located therein.

11. A process as claimed in claim 10 wherein:

said nozzle includes auxiliary passage means extending from the exterior of said nozzle within said housing to said constriction, and the passage of said gas-liquid mixture through said constriction draws a gas-liquid mixture from within the interior of said housing into said passage in the area of said constriction.

12. A process as claimed in claims 9 or 11 wherein: said gas-liquid mixture comprises water containing a reactant selected from the group consisting of oxygen and ozone.

* * * * *

UNITED STATES PATENT AND TRADEMARK OFFICE
CERTIFICATE OF CORRECTION

PATENT NO. : 4,189,363
DATED : FEBRUARY 19, 1980
INVENTOR(S) : STUART W. BEITZEL

It is certified that error appears in the above-identified patent and that said Letters Patent are hereby corrected as shown below:

On the Abstract page of the patent, under Section (75) INVENTOR correct "Stuart S. Beitzel" to read--Stuart W. Beitzel--.

Column 5, line 25, ".05" should read --0.5--.

Column 6, line 9, "as" should read --a--.

Column 7, line 26, "purity" should read --purify--.

Column 7, line 40, correct the spelling of --apparatus--.

Signed and Sealed this

Twentieth Day of January 1981

[SEAL]

Attest:

RENE D. TEGTMEYER

Attesting Officer

Acting Commissioner of Patents and Trademarks